United States Patent
Roteliuk

(10) Patent No.: US 7,452,333 B2
(45) Date of Patent: *Nov. 18, 2008

(54) ARTERIAL PRESSURE-BASED, AUTOMATIC DETERMINATION OF A CARDIOVASCULAR PARAMETER

(75) Inventor: Luchy Roteliuk, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 501 days.

This patent is subject to a terminal disclaimer.

(21) Appl. No.: 10/890,887

(22) Filed: Jul. 14, 2004

(65) Prior Publication Data

US 2005/0124904 A1    Jun. 9, 2005

Related U.S. Application Data

(63) Continuation-in-part of application No. 10/728,705, filed on Dec. 5, 2003, now Pat. No. 7,220,230.

(51) Int. Cl.
*A61B 5/02* (2006.01)

(52) U.S. Cl. .................................................. 600/485

(58) Field of Classification Search .......... 600/481–507
See application file for complete search history.

(56) References Cited

U.S. PATENT DOCUMENTS

| | | | |
|---|---|---|---|
| 4,236,527 A | 12/1980 | Newbower et al. | |
| 4,429,701 A | 2/1984 | Goor et al. | |
| 4,507,974 A | 4/1985 | Yelderman | |
| 4,535,774 A | 8/1985 | Olson | |
| 4,562,843 A | 1/1986 | Djordjevic et al. | |
| 4,595,015 A | 6/1986 | Jansen et al. | |
| 4,798,211 A | 1/1989 | Goor et al. | |
| 4,834,107 A | 5/1989 | Warner | |

(Continued)

FOREIGN PATENT DOCUMENTS

EP          393 228 A1     10/1990

(Continued)

OTHER PUBLICATIONS

Antonutto, G.; Girardos, M.; Tuniz, D.; di Prampero, P.E.; "Noninvasive assessment of cardiac output from arterial pressure profiles during exercise"; European Journal of Applied Physiology, 72(1995), 18-24.

(Continued)

*Primary Examiner*—Robert L. Nasser, Jr.
*Assistant Examiner*—Karen E Toth
(74) *Attorney, Agent, or Firm*—Gregory J. Carlin

(57) ABSTRACT

One or more cardiovascular parameters is estimated as a function of the arterial pressure waveform, in particular, using at least one statistical moment of pressure waveform having an order greater than one. Arterial compliance, the exponential pressure decay constant, vascular resistance, cardiac output, and stroke volume are examples of cardiovascular parameters that can be estimated using various aspects of the invention. In one embodiment of the invention, not only are the first four moments (mean, standard deviation, skewness, and kurtosis) of the pressure waveform used to estimate the cardiovascular parameter(s) of interest, but also heart rate, statistical moments of a set of pressure-weighted time values, and certain anthropometric patient measurements such as age, sex, body surface area, etc.

76 Claims, 2 Drawing Sheets

U.S. PATENT DOCUMENTS

| | | | |
|---|---|---|---|
| 5,101,828 A | 4/1992 | Welkowitz et al. |
| 5,146,414 A | 9/1992 | McKown et al. |
| 5,178,151 A | 1/1993 | Sackner et al. |
| 5,183,051 A | 2/1993 | Kraidin et al. |
| 5,199,438 A | 4/1993 | Pearlman |
| 5,211,177 A | 5/1993 | Chesney et al. |
| 5,241,966 A | 9/1993 | Finkelstein et al. |
| 5,265,011 A | 11/1993 | O'Rourke |
| 5,265,615 A | 11/1993 | Frank et al. |
| 5,316,004 A | 5/1994 | Chesney et al. |
| 5,390,679 A | 2/1995 | Martin |
| 5,400,793 A | 3/1995 | Wesseling |
| 5,423,323 A | 6/1995 | Orth |
| 5,526,817 A | 6/1996 | Pfeiffer et al. |
| 5,533,511 A | 7/1996 | Kaspari et al. |
| 5,535,753 A | 7/1996 | Petrucelli et al. |
| 5,584,298 A | 12/1996 | Kabal et al. |
| 5,634,467 A | 6/1997 | Nevo |
| 5,638,823 A * | 6/1997 | Akay et al. ............ 600/528 |
| 5,647,369 A | 7/1997 | Petrucelli et al. |
| 5,687,733 A | 11/1997 | McKown |
| 5,730,138 A | 3/1998 | Wang |
| 5,743,268 A | 4/1998 | Kabal et al. |
| 5,746,698 A | 5/1998 | Bos et al. |
| 5,797,395 A | 8/1998 | Martin |
| 5,830,131 A | 11/1998 | Caro et al. |
| 5,865,758 A | 2/1999 | Louzianine |
| 5,876,347 A | 3/1999 | Chesney et al. |
| 5,913,826 A | 6/1999 | Blank |
| 6,004,274 A | 12/1999 | Nolan et al. |
| 6,010,457 A | 1/2000 | O'Rourke |
| 6,017,313 A | 1/2000 | Bratteli et al. |
| 6,048,318 A | 4/2000 | Chesney et al. |
| 6,071,244 A | 6/2000 | Band et al. |
| 6,090,047 A | 7/2000 | Kass et al. |
| 6,117,087 A | 9/2000 | Kamm et al. |
| 6,141,590 A | 10/2000 | Renirie et al. |
| 6,165,130 A | 12/2000 | Chio |
| 6,216,094 B1 | 4/2001 | Fox Linton et al. |
| 6,224,585 B1 | 5/2001 | Pfeiffer |
| 6,228,033 B1 | 5/2001 | Kööbi et al. |
| 6,231,498 B1 | 5/2001 | Pfeiffer et al. |
| 6,270,461 B1 | 8/2001 | Chio |
| 6,290,651 B1 | 9/2001 | Chesney et al. |
| 6,315,735 B1 | 11/2001 | Joeken |
| 6,348,038 B1 | 2/2002 | Band et al. |
| 6,394,958 B1 | 5/2002 | Bratteli et al. |
| 6,471,655 B1 | 10/2002 | Baura |
| 6,485,431 B1 | 11/2002 | Campbell |
| 6,514,211 B1 | 2/2003 | Baura |
| 6,554,774 B1 | 4/2003 | Miele |
| 6,676,608 B1 | 1/2004 | Keren |
| 7,220,230 B2 * | 5/2007 | Roteliuk et al. ......... 600/485 |
| 2002/0022785 A1 | 2/2002 | Romano |
| 2002/0052553 A1 | 5/2002 | Shalman et al. |
| 2003/0060722 A1 | 3/2003 | Pfeiffer et al. |
| 2003/0191400 A1 | 10/2003 | Shalman et al. |
| 2004/0087863 A1 | 5/2004 | Eide |
| 2004/0158163 A1 | 8/2004 | Cohen et al. |

FOREIGN PATENT DOCUMENTS

| | | |
|---|---|---|
| EP | 420 085 A2 | 4/1991 |
| EP | 448 979 A1 | 10/1991 |
| EP | 564 492 B1 | 10/1993 |
| EP | 569 506 B1 | 11/1993 |
| EP | 642 760 A1 | 3/1995 |
| EP | 947 160 A1 | 10/1999 |
| EP | 947 941 A2 | 10/1999 |
| EP | 1 236 435 B1 | 9/2002 |
| WO | WO 90/03145 | 4/1990 |
| WO | WO 90/11042 | 10/1990 |
| WO | WO 92/06633 | 4/1992 |
| WO | WO 92/11804 | 7/1992 |
| WO | WO 92/12669 | 8/1992 |
| WO | WO 94/14372 | 7/1994 |
| WO | WO 94/22363 | 10/1994 |
| WO | WO 95/16391 | 6/1995 |
| WO | WO 97/24982 | 7/1997 |
| WO | WO 98/19594 | 5/1998 |
| WO | WO 99/02086 | 1/1999 |
| WO | WO 00/64339 | 11/2000 |

OTHER PUBLICATIONS

Fagard, R. and Conway, 3 (1990); "Measurement of cardiac output: Fick principle using catheterization"; Eur. Heart J. 11, Suppl. I, pp. 1-5.

Ganz, W. and Swan, H.J.C. (1972); "Measurement of blood flow by thermodilution"; Am. J. Cardiol. 29, pp. 241-246.

Goedje, O.; Hoeke, K.; Lichtwark-Aschoff, M.; Faltchauser, A.; Lamm, P.; Reichart, B.; "Continuous cardiac output by femoral arterial thermodilution calibrated pulse contour analysis: Comparison with pulmonary arterial thermodilution"; Critical Care Medicine, 27 (1999), 2407-2412.

Gratz, I; Kraidin, J.; Jacobi, A.G.; deCastro, N.G.; Spagna, P.; Larijani, G.E.; "Continuous noninvasive cardiac output as estimated from the pulse contour curve"; Journal of Clinical Monitoring, 8 (1992), 20-27.

Harms, M.P.M.; Wesseling, K.H.; Pott, F., et al. (1999); "Continuous stroke volume monitoring by modelling flow from non invasive measurement of arterial pressure in humans under orthostatic stress"; Clin. Sci. 97, pp. 291-301.

Houtman, S.; Oeseburg, B. and Hopman, M.T.E. (1999); "Non invasive cardiac output assessment during moderate exercise: pulse contour compared with C02 rebreathing"; Clin. Physiol. 19, pp. 230-237.

Irlbeck, M.; Forst, H.; Briegel, J.; Haller, M.; Peter, K.; "Die kontinuierliche Messung des Herzzeitvolumens mit der Pulskonturanalyse; Der Anaesthesist"; 44 (1995), 493-500.

Jansen, J.R.; Wesseling, K.H.; Settels, J.J.; Schreuder, J.J.; "Continuous cardiac output monitoring by pulse contour during cardiac surgery"; European Heart Journal, 11 (1990), 26-32.

Jansen, J.R.C.; Schreuder, J.J.; Mulier, J.P.; Smith, N.T.; Settels, J.J. and Wesseling, K.H.; "A comparison of cardiac output derived from the arterial pressure wave against thermodilution in cardiac surgery patients"; British Journal of Anaesthesia, 87 (2) (2001), 212-22.

Jellema, W.T.; Wesseling, K.H.; Groeneveld, A.B.J; Stoutenbeek, C.P.; Thjis, L.G. and van Lieshout, J.J. (1999); "Continuous cardiac output in septic shock by simulating a model of the thermodilution"; Anesthesiology 90, pp. 1317-1328.

Jellema, W.T.; Imholz, B.P.M.; van Goudoever, J.; Wesseling, K.H. and van Lieshout, J.J. (1996): "Finger arterial versus intrabrachial pressure and continuous cardiac output during head up tilt testing in healthy subjects", Clin. Sci. 91, pp. 193-200.

Langewouters, G.J.; Wesseling, K.H. and Goedhard, W.J.A. (1984); "The static elastic properties of 45 human thoracic and 20 abdominal aortas in vitro and the parameters of a new model"; J. Biomech. 17, pp. 425-435.

McKay, W.P.; Gregson, P.H.; McKay, B.W.; Militzer, J.; "Sternal acceleration ballistocardiography and arterial pressure wave analysis to determine stroke volume"; Clinical and Investigative Medicine, 22 (1999), 4-14.

Martin, J.F.; Volfson, L.B.; Kirzon-Zolin, V.V.; Schukin, V.G.; "Application of pattern recognition and image classification techniques to determine continuous cardiac output from the arterial pressure waveform"; IEEE Transactions on Biomedical Electronics, 41 (1994), 913-920.

Romano, Salvatore M.; Pistolesi, Massimo; "Assessment of cardiac output from systemic arterial pressure in humans"; Crit Care Med 2002 vol. 30, No. 8, pp. 1834-1841.

Sprangers, R.L.; Wesseling, K.H.; Imholz, A.L.; Imholz, B.P. and Wieling, W. (1991); "Initial blood pressure fall on stand up and exercise explained by changes in total peripheral resistance"; J. Appl. Physiol. 70, pp. 523-530.

Stok, W. J.; Baisch, F.; Hillebrecht, A.; Schulz, H. and Karemaker, J.M. (1993); "Noninvasive cardiac output measurement by arterial pulse analysis compared to inert gas rebreathing"; J. Appl. Physiol. 74, pp. 2687-2693.

Stok, W.J.; Stringer, R.C.O. and Karemaker, J.M. (1999); "Noninvasive cardiac output measurement in orthostasis: pulse contour analysis compared with acetylene rebreathing"; J. Appl. Physiol. 87, pp. 2266-2273.

Wesseling. K.H.; Dc Wit, B.; Weber, J.A.P. and Smith, N.T. (1983); "A simple device for the continuous measurement of cardiac output. Its model basis and experimental verification"; Adv. Cardiol. Phys. 5, Suppl. II, pp. 16 52.

Wesseling; K.H.; Jansen, J.R.C.; Settels, J.J. and Schreuder, J.J. (1993); "Computation of aortic flow from pressure in humans using a nonlinear, three element model"; J. Appl. Physiol. 74, pp. 2566-2573.

* cited by examiner ial. Pressure-Based, Automatic Determination of a Cardiovascular Parameter

CROSS-REFERENCE TO RELATED APPLICATIONS

This application is a continuation-in-part and claims priority of U.S. patent application Ser. No. 10/728,705 filed 5 Dec. 2003 now U.S. Pat. No. 7,220,230.

BACKGROUND OF THE INVENTION

1. Field of the Invention

This invention relates to hemodynamic monitoring and in particular to estimation of at least one cardiovascular parameter, such as arterial compliance or resistance, pressure decay, cardiac output or stroke volume (SV), etc., as well as to a system that implements the method.

2. Background Art

Cardiac output (CO) is an important indicator not only for diagnosis of disease, but also for "real-time" monitoring of the condition of both human and animal subjects, including patients. Few hospitals are therefore without some form of conventional equipment to monitor cardiac output. Many suitable techniques—both invasive and non-invasive, as well as those that combine both—are in use and even more have been proposed in the literature.

One invasive way to determine cardiac output (or, equivalently, SV) is to mount some flow-measuring device on a catheter, and then to thread the catheter into the subject and to maneuver it so that the device is in or near the subject's heart. Some such devices inject either a bolus of material or energy (usually heat) at an upstream position, such as in the right atrium, and determine flow based on the characteristics of the injected material or energy at a downstream position, such as in the pulmonary artery. Patents that disclose implementations of such invasive techniques (in particular, thermodilution) include:

U.S. Pat. No. 4,236,527 (Newbower et al., 2 Dec. 1980);
U.S. Pat. No. 4,507,974 (Yelderman, 2 Apr. 1985);
U.S. Pat. No. 5,146,414 (McKown, et al., 8 Sep. 1992); and
U.S. Pat. No. 5,687,733 (McKown, et al., 18 Nov. 1997).

Still other invasive devices are based on the known Fick technique, according to which CO is calculated as a function of oxygenation of arterial and mixed venous blood. In most cases, oxygenation is sensed using right-heart catheterization. There have, however, also been proposals for systems that measure arterial and venous oxygenation non-invasively, in particular, using multiple wavelengths of light, but to date they have not been accurate enough to allow for satisfactory CO measurement on actual patients.

Invasive techniques have obvious disadvantages, the main one of which is of course that catheterization of the heart is potentially dangerous, especially considering that the subjects (especially intensive care patients) on which it is performed are often already in the hospital because of some actually or potentially serious condition. Invasive methods also have less obvious disadvantages: Some techniques such as thermodilution rely on assumptions, such as uniform dispersion of the injected heat, that affect the accuracy of the measurements depending on how well they are fulfilled. Moreover, the very introduction of an instrument into the blood flow may affect the value (for example, flow rate) that the instrument measures.

There has therefore been a long-standing need for some way of determining CO that is both non-invasive—or at least as minimally invasive as possible—and accurate. One blood characteristic that has proven particularly promising for accurately determining CO non-invasively is blood pressure.

Most known blood-pressure-based systems rely on the so-called pulse contour method (PCM), which calculates as estimate of CO from characteristics of the beat-to-beat pressure waveform. In the PCM, "Windkessel" (German for "air chamber") parameters (characteristic impedance of the aorta, compliance, and total peripheral resistance) are used to construct a linear or non-linear, hemodynamic model of the aorta. In essence, blood flow is analogized to a flow of electrical current in a circuit in which an impedance is in series with a parallel-connected resistance and capacitance (compliance). The three required parameters of the model are usually determined either empirically, through a complex calibration process, or from compiled "anthropometric" data, that is, data about the age, sex, height, weight, etc., of other patients or test subjects. U.S. Pat. No. 5,400,793 (Wesseling, 28 Mar. 1995) and U.S. Pat. No. 5,535,753 (Petrucelli, et al., 16 Jul. 1996) are representative of systems that rely on a Windkessel circuit model to determine CO.

PCM-based systems can monitor CO more or less continuously, with no need for a catheter (usually right heart) to be left in the patient. Indeed, some PCM systems operate using blood pressure measurements taken using a finger cuff. One drawback of PCM, however, is that it is no more accurate than the rather simple, three-parameter model from which it is derived; in general, a model of a much higher order would be needed to faithfully account for other phenomena, such as the complex pattern of pressure wave reflections due to multiple impedance mis-matches caused by, for example, arterial branching. Because the accuracy of the basic model is usually not good enough, many improvements have been proposed, with varying degrees of complexity.

The "Method and apparatus for measuring cardiac output" disclosed by Salvatore Romano in U.S. Published Patent Application 20020022785 A1 (21 Feb. 2002, "Method and apparatus for measuring cardiac output") represents a different attempt to improve upon PCM techniques by estimating SV, either invasively or non-invasively, as a function of the ratio between the area under the entire pressure curve and a linear combination of various components of impedance. In attempting to account for pressure reflections, the Romano system relies not only on accurate estimates of inherently noisy derivatives of the pressure function, but also on a series of empirically determined, numerical adjustments to a mean pressure value.

At the core of several methods for estimating CO is an expression of the form $CO=HR*(K*SV_{est})$ where HR is the heart rate, $SV_{est}$ is the estimated stroke volume, and K is a scaling factor related to arterial compliance. Romano and Petrucelli, for example, rely on this expression, as do the apparatuses disclosed in U.S. Pat. 6,071,244 (Band, et al., 6 Jun. 2000); and U.S. Pat. No. 6,348,038 (Band, et al., 19 Feb. 2002).

Another expression often used to determines CO is $CO=MAP*C/tau$ where MAP is mean arterial pressure, tau is an exponential pressure decay constant, and C, like K, is a scaling factor related to arterial compliance as K. U.S. Pat. No. 6,485,431 (Campbell, 26 Nov. 2002) discloses one apparatus that uses such an expression.

The accuracy of these methods depends on how the compliance factors K and C are determined. In other words, an accurate estimate of compliance (or of some other value functionally related to compliance) is required. For example, Langwouters ("The Static Elastic Properties of 45 Human Thoracic and 20 Abdominal Aortas in vitro and the Parameters of a New Model," J. Biomechanics, Vol. 17, No. 6, pp. 425-435, 1984) measured vascular compliance per unit length in human aortas and related it to patient age and sex. An aortic length was then found to be proportional to patient weight and height. A nomogram, based on this patient information, was then derived and used in conjunction with information derived from an arterial pressure waveform to improve an estimate of the compliance factor.

The different prior art apparatuses identified above each suffer from one or more drawbacks. The Band apparatus, for example, requires an external calibration using an independent measure of CO to determine a vascular impedance-related factor that is then used in CO calculations. U.S. Pat. No. 6,315,735 (Joeken, et al., 13 Nov. 2001) describes another device with the same shortcoming.

Wesseling (U.S. Pat. No. 5,400,793, 28 Mar. 1995) and Campbell each attempt to determine a vascular compliance-related factor from anthropometric data such as patient height, weight, sex, age, etc. These methods rely on relationships that are determined from human nominal measurements and do not apply robustly to a wide range of patients.

Petrucelli attempts to determine a vascular compliance-related factor from not only anthropometric data, but also from a characteristic of the arterial pressure waveform. Using only age, height, weight, systolic pressure and diastolic pressure, Petrucelli's method has proven unreliable in a wide range of patients.

Romano attempts to determine a vascular impedance-related factor solely from features of the arterial pressure waveform, and thus fails to take advantage of known relationships between patient characteristics and compliance. In other words, by freeing his system of a need for anthropometric data, Romano also loses the information contained in such data. Moreover, Romano bases several intermediate calculations on values of the derivatives of the pressure waveform. As is well known, however, such estimates of derivatives are inherently noisy. Romano's method has, consequently, proved unreliable.

What is needed is a system and method of operation for more accurately and robustly estimating cardiovascular parameters such as arterial compliance (K or C) or resistance, tau, or values computed from these parameters, such as SV and CO. This invention meets this need.

SUMMARY OF THE INVENTION

Given an invasively or non-invasively measured arterial pressure waveform of a subject, the invention operates on one or more of three sets of input data: 1) one or more statistical moments (mean, standard deviation, skewness, kurtosis, etc.) of the digitized arterial pressure waveform.; 2) one or more statistical moments of a set of pressure-weighted time values, each pressure-weighted time value corresponding to the product of a sensing time, relative to an initial time, and arterial pressure at the sensing time; and 3) a set of anthropometric values (heart rate, body surface area, age, sex, height, weight, etc.) to estimate one or more of a set of cardiovascular parameters including a value of arterial compliance, stroke volume, cardiac output, vascular resistance, a pressure decay constant, or any other cardiovascular parameter that can be derived from any of these.

DETAILED DESCRIPTION

Introduction

In broadest terms, the invention involves the determination of a cardiovascular parameter such as the compliance factor (such as K or C in the formulas given above) as a multi-parameter function of not only mean arterial pressure, which corresponds the first moment of the blood pressure waveform, but also of one or more higher-order moments of the waveform as well. Patient-specific data is preferably also incorporated in the multi-parameter function as well.

The organization of this description is: First, the theoretical basis of the invention is discussed. This is followed by an explanation of the main steps of a method to use the theory, then a description of a system that implements the method.

The invention may be used to advantage with any type of subject, whether human or animal. Because it is anticipated that the most common use of the invention will be on humans in a diagnostic setting, the invention is described below primarily in use with a "patient." This is by way of example only, however—it is intended that the term "patient" should encompass all subjects, both human and animal, regardless of setting.

Pressure Waveforms

Figure 1:
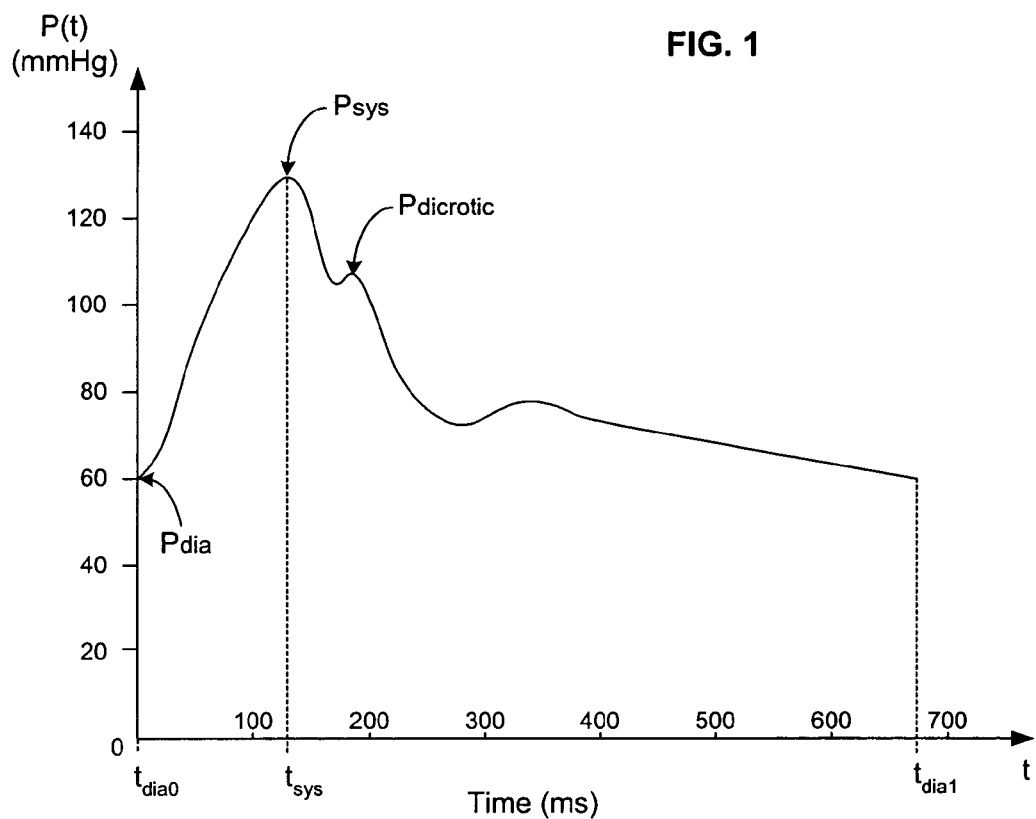
FIG. 1 is an illustrative example of a complex blood pressure curve over one beat-to-beat heart cycle.

FIG. 1 illustrates an example of the waveform P(t) of arterial pressure taken over a single heart cycle, here, from the point of diastolic pressure $P_{dia}$ at time $t_{dia0}$, through the time $t_{sys}$ of systolic pressure $P_{sys}$, to a time $t_{dia1}$ at which the blood pressure once again reaches $P_{dia}$.

According to the invention, P(t), or any signal that is proportional to P(t), may be measured at any point in the arterial tree, either invasively or non-invasively. If invasive instruments are used, in particular, catheter-mounted pressure transducers, then any artery may be used as a measurement point. Placement of non-invasive transducers will typically be dictated by the instruments themselves—the placement of finger cuffs, upper arm pressure cuffs, and earlobe clamps should be obvious. Regardless of the instrument, it will ultimately produce, or cause to be produced, an electric signal corresponding (for example, proportional) to P(t).

Figure 2:
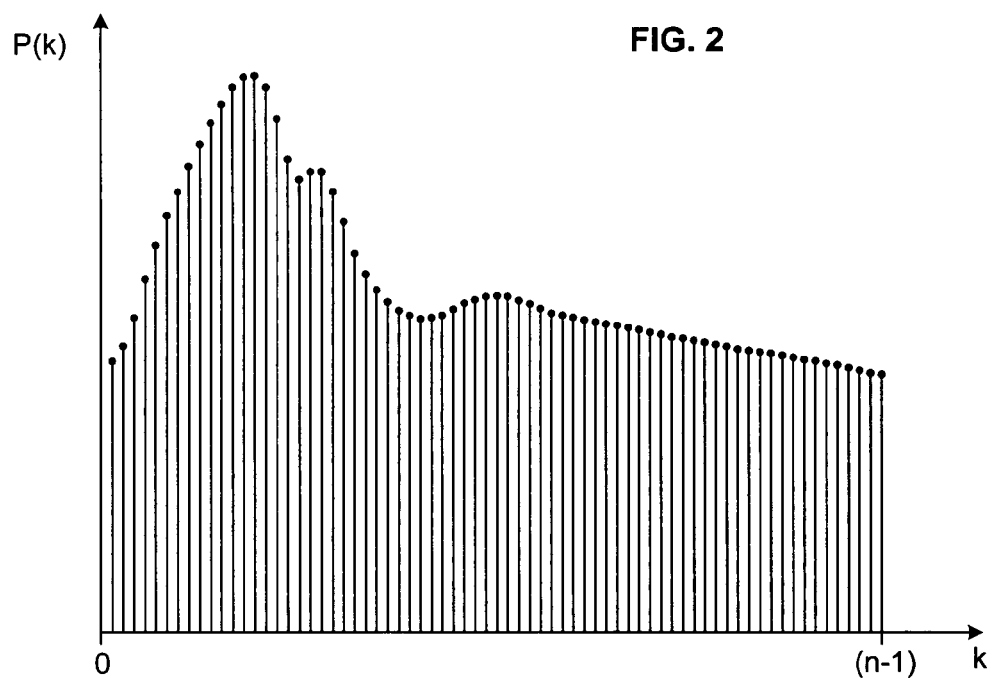
FIG. 2 illustrates a discrete-time representation of the pressure waveform in FIG. 1.

As is well known, and as is illustrated in FIG. 2, analog signals such as P(t) can be digitized into a sequence of digital values using any standard analog-to-digital converter (ADC). In other words, P(t), $t0 \leq t \leq tf$, can be converted, using known methods and circuitry, into the digital form P(k), k=0, (n−1), where t0 and tf are initial and final times, respectively, of the measurement interval and n is the number of samples of P(t) to be included in the calculations, distributed usually evenly over the measurement interval.

Moments

Now consider an ordered collection of m values, that is, a sequence Y(i), where i=0, . . . , (m−1). As is well known from the field of statistics, the first four moments $\mu_1$, $\mu_2$, $\mu_3$, and $\mu_4$ of Y(i) can be calculated using know formulas, where $\mu_1$ is the mean (that is, arithmetic average), $\mu_2 = \sigma^2$ is the variation, that is, the square of the standard deviation $\sigma$; $\mu_3$ is the skewness, and $\mu_4$ is the kurtosis. Thus:

$\mu_1 Y_{avg} = 1/m * \text{SUM}(Y(i))$ (Formula 1)

$\mu_2 = \sigma^2 = 1/(m-1) * \text{SUM}(Y(i) - Y_{avg})^2$ (Formula 2)

$$\mu_3 = 1/(m-1)*\text{SUM}[(Y(i)-Y_{avg})/\sigma]^3 \quad \text{(Formula 3)}$$

$$\mu_4 = 1/(m-1)*\text{SUM}[(Y(i)-Y_{avg})/\sigma]^4 \quad \text{(Formula 4)}$$

Note that, in general, the β-th moment $\mu_\beta$ can be expressed as:

$$\mu_\beta = 1(m-1)*1/\sigma^\beta*\text{SUM}[(Y)(i)-Y_{avg})]^\beta$$

where i=0, ..., (m−1). Note also that the discrete-value formulas for the second through fourth moments usually scale by 1/(m−1) instead of 1/m for well-known statistical reasons.

As is explained further below, the preferred embodiment of the invention computes a compliance factor as a function not only of the four moments of the pressure waveform P(k), but also of a pressure-weighted time vector. Although the statistical concepts expressed in Formulas 1-4 above are well understood, as far as the inventor is aware, only the first moment $\mu_1$ of the pressure waveform, which corresponds to mean arterial pressure MAP, is used directly in the prior art in calculations relating to arterial compliance. Use of only MAP is a severe and wasteful limitation in that MAP reduces all the accumulated information of the pressure waveform P(k) into a single number, which provides no information at all about the shape of the waveform other than its average amplitude.

Standard deviation σ provides one level of shape information in that the greater a is, the more "spread out" the function (that, is, sequence) Y(i) is, that is, the more it tends to deviate from the mean. Of course, to get the standard deviation σ the system simply takes the square root of the variation $\sigma^2$.

Although the standard deviation provides some shape information, its shortcoming can be easily understood by considering the following: the mean and standard deviation will not change if the order in which the values making up the sequence Y(i) is "reversed," that is, Y(i) is reflected about the i=0 axis and shifted so that the value Y(m−1) becomes the first value in time.

Skewness is a measure of lack of symmetry and indicates whether the left or right side of the function Y(i), relative to the statistical mode, is heavier than the other. A positively skewed function rises rapidly, reaches its peak, then falls slowly. The opposite would be true for a negatively skewed function. The point is that the skewness value includes shape information not found in the mean or standard deviation values—in particular, it indicates how rapidly the function initially rises to its peak and then how slowly it decays. Two different functions may have the same mean and standard deviation, but they will then only rarely have the same skewness.

Kurtosis is a measure of whether the function Y(i) is more peaked or flatter than a normal distribution. Thus, a high kurtosis value will indicate a distinct peak near the mean, with a drop thereafter, followed by a heavy "tail." A low kurtosis value will tend to indicate that the function is relatively flat in the region of its peak. A normal distribution has a kurtosis of 3.0; actual kurtosis values are therefore often adjusted by 3.0 so that the values are instead relative to the origin.

Pressure Waveform Moments

According to the preferred embodiment of the invention, the first four moments $\mu_{1P}$, $\mu_{2P}$, $\mu_{3P}$, and $\mu_{4P}$ of the pressure waveform P(k) are calculated and used in the computation of the compliance factor, where $\mu_{1P}$ is the mean, $\mu_{2P} = \sigma_P^2$ is the variation, that is, the square of the standard deviation $\sigma_P$; $\mu_{3P}$ is the skewness, and $\mu_{4P}$ is the kurtosis, where all of these moments are based on the pressure waveform P(k). Formulas 1-4 above may be used to calculate these values after substituting P for Y, k for i, and n for m.

Formula 2 above provides the "textbook" method for computing a standard deviation. Other, more approximate methods may also be used. For example, at least in the context of blood pressure-based measurements, the inventor has discovered that a rough approximation to $\sigma_P$ can be had by dividing by three the difference between the maximum and minimum measured pressure values, and that the maximum or absolute value of the minimum of the first derivative of the P(t) with respect to time is generally proportional to $\sigma_P$.

Pressure-Weighted Time Moments

As FIG. 2 illustrates, at each discrete time k, the corresponding measured pressure will be P(k). The values k and P(k) can be formed into a sequence T(j) that corresponds to a histogram, meaning that each P(k) value is used as a "count" of the corresponding k value. By way of a greatly simplified example, assume that the entire pressure waveform consists of only four measured values P(1)=25, P(2)=50, P(3)=55, and P(4)=35. This could then be represented as a sequence T(j) with 25 ones, 50 twos, 55 threes, and 35 fours:

T(j)=1, 1, ..., 1, 2,2, ..., 2, 3,3, ..., 3, 4,4, ..., 4

This sequence would thus have 25+50+55+35=165 terms.

Moments may be computed for this sequence just as for any other. For example, the mean (first moment) is:

$$\mu_{1T} = (1*25+2*50+3*55+4*35)/165 = 430/165 = 2.606$$

and the standard deviation $\sigma_T$ is the square root of the variation $\mu_{2T}$:

$$\text{SQRT}[1/164*25(1-2.61)^2+50(2-2.61)^2+55(3-2.61)^2+35(4-2.61)^2] = 0.985$$

The skewness $\mu_{3T}$ and kurtosis $\mu_{4T}$ can be computed by similar substitutions in Formulas 3 and 4, respectively:

$$\mu_{3T} = \{1/(164)*(1/\sigma_T^3)\text{SUM}[P(k)*(k-\mu_{1T})^3]\}$$

$$\mu_{4T} = \{1/(164)*(1/\sigma_T^4)\text{SUM}[P(k)*(k-\mu_{1T})^4]\}$$

where k=1, ..., (m−1).

As these formulas indicate, this process in effect "weights" each discrete time value k by its corresponding pressure value P(k) before calculating the moments of time. The sequence T(j) has the very useful property that it robustly characterizes the timing distribution of the pressure waveform: Reversing the order of the pressure values P(k) will in almost all cases cause even the mean of T(j) to change, as well as all of the higher-order moments. Moreover, the secondary "hump" that normally occurs at the dicrotic pressure $P_{dicrotic}$ also noticeably affects the value of kurtosis $\mu_{4T}$; in contrast, simply identifying the dicrotic notch in the prior art, such as in the Romano method, requires noisy calculation of at least one derivative.

Parameter Set

In one tested embodiment of the invention, all four of the pressure waveform and pressure-weighted time moments are used to compute a compliance factor K that can be used either on its own or in other formulas, such as those given above for calculating cardiac output. Additional values are preferably also included in the computation to take other known characteristics into account. In one prototype of the invention, for example, the heart rate HR (or period of R-waves), the body surface area BSA, as well as a compliance value $K_{prior}$ calculated using a know method such as described by Langwouters, which computes compliance as a polynomial function of the pressure waveform and the patient's age and sex. Thus, in the tested embodiment:

$$K=K(HR, K_{prior}, BSA, \mu_{1P}, \sigma_P, \mu_{3P}, \mu_{4P}, \mu_{1T}, \sigma_T, \mu_{3T}, \mu_{4T})$$

Depending on the needs of a given implementation of the invention and using known experimental methods, one might also choose not to include either skewness or kurtosis, or one might also include even higher order moments. Tests using both sets of all of the first four statistical moments have proven successful in contributing to an accurate and robust estimate of compliance. Moreover, other anthropometric parameters than HR and BSA may be used in addition, or instead, and other methods may be used to determine $K_{prior}$, which may even be omitted altogether. The example methodology described below for computing a current compliance value may be adjusted in a known manner to reflect the increased, decreased, or altered parameter set.

Approximating Function—Coefficient Determination

Once the parameter set for computing K has been assembled, it must still be related to something that is known. Recall the two standard expressions for calculating CO given above:

$$CO = HR \cdot K \cdot SV_{est}$$

$$CO = MAP \cdot C/\tau$$

Existing devices and methods, including invasive techniques such as thermodilution, may be used to determine CO, HR and $SV_{est}$ for a population of test or reference subjects. (MAP and tau can similarly be determined using known techniques.) For each subject, anthropometric data such as age, weight, BSA, height, etc. can also be recorded. This creates a suite of CO measurements, each of which is a function (initially unknown) of the component parameters of K. An approximating function can therefore be computed, using known numerical methods, that best relates the parameters to K (or C) given the suite of CO measurements in some predefined sense. One well understood and easily computed approximating function is a polynomial. In one successfully tested implementation of the invention, a standard multivariate fitting routine was used to generate the coefficients of a polynomial that gave a value of K for each set of parameters HR, $K_{prior}$, BSA, $\mu_{1P}, \sigma_P, \mu_{3P}, \mu_{4P}, \mu_{1T}, \sigma_T, \mu_{3T}, \mu_{4T}$ In one implementation of the invention, K was computed as follows:

$$K = [A_1 \ A_2 \ \ldots \ A_n] * \begin{bmatrix} X_1 \\ X_2 \\ \ldots \\ X_n \end{bmatrix}$$

where $$X_{n,1} = \prod_m \left( [v_1 \ v_2 \ \ldots \ v_m] \wedge \begin{bmatrix} P_{1,1} & \ldots & P_{1,n} \\ \ldots & \ldots & \ldots \\ P_{n,1} & \ldots & P_{n,n} \end{bmatrix} \right)$$

The coefficients "A" and the exponent matrix "P" were determined to be as follows by multivariate least-squares regression using data collected from human subjects:

$$A = [0.085831 \ 4.7797 \ -0.74519 \ 1.1204 \ 0.00010546 \ 1.525 \ -0.010744]$$

$$P = \begin{bmatrix} 1 & 0 & 2 & 0 & 0 & 0 & 0 & 0 & 0 & 0 \\ 0 & 0 & -2 & 0 & 0 & 0 & 0 & 0 & 0 & 0 \\ 0 & -1 & -1 & 0 & 0 & 0 & 0 & 0 & 0 & 0 \\ 0 & 1 & -1 & 0 & -2 & 1 & 0 & 0 & 0 & 0 \\ 0 & 1 & -1 & 0 & 0 & 0 & 2 & 0 & 0 & 2 \\ 0 & 0 & 0 & 2 & 0 & 0 & 1 & 0 & 0 & -2 \\ 0 & 2 & 0 & 0 & 0 & 0 & 2 & 0 & 0 & 0 \end{bmatrix}$$

The expression for K can be written in the following form:

$$K = \frac{8.5831 * v_1 * v_3^2}{100} + \frac{4.7797}{v_3^2} - \frac{0.74519}{v_2 * v_3} + \frac{1.1204 * v_2 * v_6}{v_3 * v_5^2} + \frac{1.0546 * v_2 * v_8^2 * v_{11}^2}{10000 * v_3} + \frac{1.525 * v_4^2 * v_7}{v_{11}^2} - \frac{1.0744 * v_2^2 * v_7^2}{100}$$

in which the factors "v" are defined as:

$$v_1 = \frac{600}{HR}$$

$$v_2 = \frac{100 * B1(\text{sex})}{\pi * \alpha * (1 + ((\mu_{1P} - B2(\text{sex}) + B3(\text{sex}) * \text{age})/\alpha)^2)}$$

where $\alpha = 57 - 0.44 * \text{age}$ $v_3 = BSA = 0.007184 * \text{weight}^{0.425} * \text{height}^{0.725}$ $v_4 = \mu_{1P}/100$ $v_5 = \sigma_P/10$ $v_6 = \mu_{3P}$ $v_7 = \mu_{4P} + 3$ $v_8 = \mu_{1T}/100$ $v_9 = \sigma_T/10$ $v_{10} = \mu_{3T}$ $v_{11} = \mu_{4T} + 3$ where:
B(male)=[5.62 76 0.89]
B(female)=[4.12 73 0.89]
Bi(sex) is element i of the respective array for the indicated sex.

Note that, in this implementation, the inventor chose to restrain the regression to at most four parameters per regression variable, with each parameter having an order (here: exponent) no greater than two. Thus, each row of the matrix P has at most four non-zero terms, with the absolute value of the each element of P being at most two. This was done for the sake of numerical stability and accuracy, even though it also meant that $v_9$ and $v_{10}$ were not included in the optimization. The expression for K therefore became a second-order curve in nine-dimensional parameter space. Other designers may choose a different number of parameters, however, or order, depending on which routine they choose to compute an estimate of K. These design choices are well understood by those who develop methods of estimating cardiovascular parameters. The point is that all computed moments may be used, but all are not necessarily required by the invention.

Furthermore, it may be possible to generate the approximating function for K (or some other cardiovascular parameter) even without any moments of the pressure alone, that is, without $\mu_{1P}$, $\sigma_P$, $\mu_{3P}$, and $\mu_{4P}$, based solely on one or more moments of the pressure-weighted time values $\mu_{1T}$, $\sigma_T$, $\mu_{3T}$, with or without anthropometric (or anthropomorphically derived) values such as HR, $K_{prior}$, BSA. Normal experimentation may be applied to determine which moments and parameters will yield satisfactory results in any given application of the invention.

By entering actual measured or computed values of $v_1 \ldots v_{11}$ into the approximating function, one obtains an estimate of the compliance factor K. If the compliance factor is the value of interest, then it may be presented to the user in any desired, conventional manner. In most implementations, however, the compliance factor is itself an intermediate parameter intended for use in the determination of some other characteristic cardiac value such as SV or CO.

The inventor has also observed that the compliance factor C and the compliance factor K are related by a gain factor of approximately six, such that $K \approx 6*C$. any expression for computing K can therefore easily be modified to estimate C.

The methodology described above may be applied even where the cardiovascular parameter of interest is something other than arterial compliance. Thus, the invention may be applied to estimate any cardiovascular parameter if a set of clinically measured variables is related to it; the relationship is characterized by using a known numerical method to determine an approximation function (having at least one higher-order moment of the pressure waveform as a variable) for the relationship; and the actual values measured or computed are substituted for the variables of the approximating function to get a current value of the cardiovascular parameter of interest.

SV and CO Estimation

As mentioned above, the principle formula for calculating cardiac output (CO) is CO=SV·HR, where SV is stroke volume and HR is heart rate. Given HR, the problem then remains how to determine SV. Based on the observation that the pulsatility of a pressure waveform is created by the cardiac stroke volume into the arterial tree, the inventor has discovered that SV can be approximated as being proportional to the standard deviation of the arterial pressure waveform P(t), or of some other signal that itself is proportional to P(t). Thus, one way to estimate SV is to apply the relationship $SV = K \cdot \sigma_P$ from which follows that $CO = K \cdot \sigma_P \cdot HR$.

The inventor has also observed that the standard deviation $\sigma_P$ of the blood pressure measured in the femoral artery of patients just leaving surgery remains relatively constant even though their CO is increasing, whereas $\sigma_P$ measured in the radial artery increases more than expected, probably reflecting the reperfusion of minor vessels. The inventor has discovered, however, that peripheral perfusion status causes significant deviation from the normal kurtosis value of 3.0 and that the estimate of SV can be corrected for this difference by subtracting a correction factor that is proportional to the pressure kurtosis. Thus, an improved SV (and thus also CO) estimate can be had by calculating:

$$SV = K \cdot \sigma_P - \gamma \cdot (\mu_{4P} - 3)$$

Setting $\gamma = 3.0$ gave good results. Here, the value three is subtracted from $\mu_{4P}$ for centering on the origin. All of the formulas given here that involve kurtosis, however, may use $\mu_{4P}$ "as is" or be centered, as long as the formulas are modified according to the choice.

Since the invention calculates $\sigma_P$ and K, it therefore can also yield an estimate of SV every time K is estimated. By using any known device for measuring HR, the invention also provides an estimate of CO. Since the estimate of K will in general be more accurate using the invention, because it employs both patient-specific information and robust pressure waveform measurements, the estimates for SV and CO will be correspondingly improved.

In order to calculate CO, the heart rate HR (or some signal from which HR can be derived) is needed. Any of the many known instruments for measuring HR may be used. If the beginning and end times for each P(t) interval are triggered by an electrocardiogram signal, for example, then the same signal may be used to calculate HR. The measured pressure wave P(t) (in practice, P(k)) may itself be used to derive HR, for example, using standard Fast Fourier transformation or derivative analysis Estimation of tau and Vascular Resistance Now recall the standard formulas $$CO = HR * (K * SV_{est}) \text{ and}$$

$$CO = MAP * C/\text{tau} = \mu_{1P} * C/\text{tau}$$

where HR is the heart rate, $SV_{est}$ is the estimated stroke volume, MAP is mean arterial pressure ($\mu_{1P}$) and tau is the exponential pressure decay parameter that describes how P(t) decays after its peak.

Combined with the inventor's observations $$K = K \approx 6 * C \text{ and}$$

$$CO = K \cdot \sigma_P \cdot HR$$

these expressions can be combined and simplified to yield an estimate of tau itself:

$$\text{tau} = MAP/(6 * HR * \sigma_P)$$

Depending on the implementation, a unit-translation constant $\kappa$ may be needed to provide unit consistency, so that $\text{tau} = \kappa * MAP/(6 * HR * \sigma_P)$. $\kappa$ may be determined using common conversion factors.

Yet another well-known relationship is tau=R*C, where R is vascular resistance. After estimating K as described above, the invention may therefore also be used to estimate R as:

$$R = 6 * \text{tau}/K$$

Measurement Interval

The analog measurement interval, that is, the time window [t0, tf], and thus the discrete sampling interval k=0, ..., (n−1), over which each calculation period is conducted should be small enough so that it does not encompass substantial shifts in the pressure and/or time moments. Also, one could filter out low frequency variations such as respiration using a high pass filter, which would also help remove the effect of any drift in mean arterial pressure during the time window. For the sake of providing more stable and reliable readings, however, is it best to let the time window extend longer than one cardiac cycle. Preferably, the measurement interval (time window) should be a plurality of cardiac cycles, that is, beginning and ending at the same point in different cardiac cycles; this ensures that the mean pressure value used in the calculations of the various higher-order moments will use a mean pressure value $P_{avg}$ that is not biased because of incomplete measurement of a cycle.

Larger sampling windows have the advantage that the effect of perturbations such as those caused by reflections will usually be reduced, since they will be tend to "cancel out" in the calculations of means and standard deviations. An appropriate time window can be determined using normal experimental and clinical methods. Note that it would be possible for the time window to coincide with a single heart cycle, in which case mean pressure shifts will not be of concern.

As a check, the system according to the invention could also, as a separate background operation, compute at least the means, and possibly also the higher-order moments, over each cardiac cycle. If the mean cycle-to-cycle pressure shows any absolute or proportional drift greater than some threshold value, a warning signal could be generated such that the currently computed compliance, SV, CO or other estimate may be considered less reliable or discarded altogether.

It would be also possible to adjust the time window [t0, tf] according to drift in $P_{avg}$. For example, if $P_{avg}$ over a given time window differs absolutely or proportionally by more than a threshold amount from the $P_{avg}$ of the previous time window, then the time window could be reduced; stability of $P_{avg}$ could then be used to indicate that the time window can be expanded. The time window could also be expanded and contracted based on noise sources, or on a measure of SNR or variation. Limits are preferably placed on how much the time window is allowed to expand or contract and if such expansion or contraction is allowed at all, then an indication of the time interval is preferably displayed to the user.

It is not necessary for the time window to start at any particular point in the cardiac cycle. Thus, $t_0$ need not be the same as $t_{dia0}$, although this may be a convenient choice in many implementations. This means that the beginning and end of each measurement interval (that is, t0 and tf) may be triggered on almost any characteristic of the cardiac cycle, such as at times $t_{dia0}$ or $t_{sys}$, or on non-pressure characteristics such as R waves, etc. In choosing such alternate intervals, however, one should keep in mind that skewness and kurtosis are shape-dependent.

Other Inputs

Rather than measure blood pressure directly, any other input signal may be used that is proportional to blood pressure. This means that calibration may be done at any or all of several points in the calculations. For example, if some signal other than arterial blood pressure itself is used as input, then it may be calibrated to blood pressure before its values are used to calculate the various component moments, or afterwards, in which case either the resulting moment values can be scaled. In short, the fact that the invention may in some cases use a different input signal than a direct measurement of arterial blood pressure does not necessarily preclude its ability to generate an accurate compliance estimate.

System Components

Figure 3:
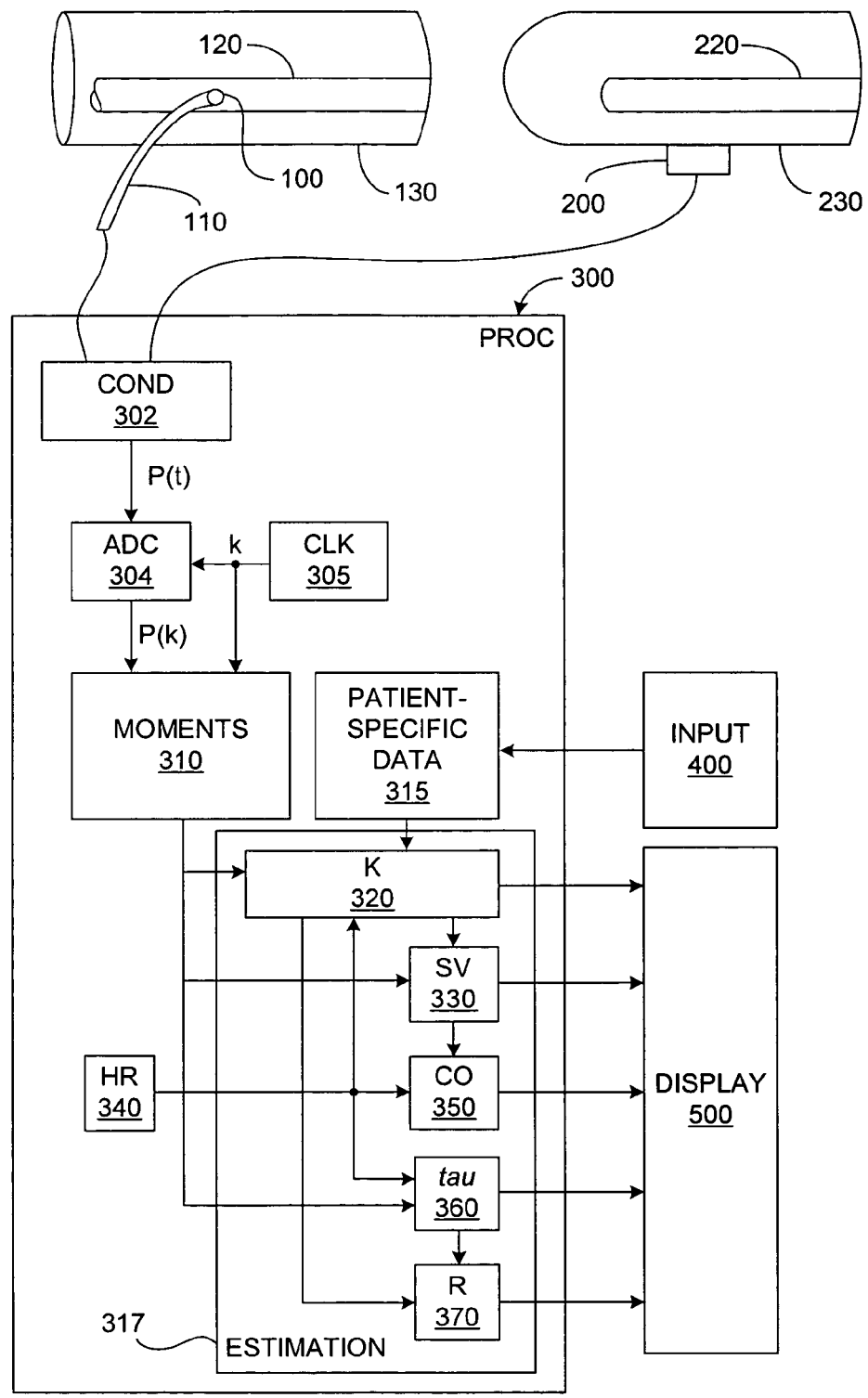
FIG. 3 is a block diagram showing the main components of a system according to the invention.

FIG. 3 shows the main components of a system that implements the method described above for sensing pressure and calculating a parameter such as compliance, SV, CO, etc. The invention may be included within an existing patient-monitoring device, or it may be implemented as a dedicated monitor. As is mentioned above, pressure, or some other input signal proportional to pressure, may be sensed in either or, indeed, both, of two ways: invasively and non-invasively. Simply because it is anticipated to be the most common implementation of the invention, the system is described as measuring arterial blood pressure as opposed to some other input signal that is converted to pressure.

FIG. 3 shows both types of pressure sensing for the sake of conciseness; in most practical applications of the invention, either one or several variations will typically be implemented. In invasive applications of the invention, a conventional pressure sensor 100 is mounted on a catheter 110, which is inserted in an artery 120 of a portion 130 of the body of a human or animal patient. Such artery could be an ascending aorta, or pulmonary artery, or, in order to reduce the level of invasiveness, the artery 120 could be peripheral, such as the femoral, radial or brachial artery. In the non-invasive applications of the invention, a conventional pressure sensor 200, such as a photo-plethysmographic blood pressure probe, is mounted externally in any conventional manner, for example using a cuff around a finger 230 or a transducer mounted on the wrist of the patient. FIG. 3 schematically shows both types.

The signals from the sensors 100, 200 are passed via any known connectors as inputs to a processing system 300, which includes one or more processors and other supporting hardware and system software (not shown) usually included to process signals and execute code. The invention may be implemented using a modified, standard, personal computer, or it may be incorporated into a larger, specialized monitoring system. In this invention, the processing system 300 also may include, or is connected to, conditioning circuitry 302 which performs such normal signal processing tasks as amplification, filtering, ranging, etc., as needed, as well as the optional high pass filtering mentioned above. The conditioned, sensed input pressure signal P(t) is then converted to digital form by a conventional analog-to-digital converter ADC 304, which has or takes its time reference from a clock circuit 305. As is well understood, the sampling frequency of the ADC 304 should be chosen with regard to the Nyquist criterion so as to avoid aliasing of the pressure signal; this procedure is very well known in the art of digital signal processing. The output from the ADC 304 will be the discrete pressure signal P(k), whose values may be stored in conventional memory circuitry (not shown).

The values P(k) are passed to (usually, accessed from memory by) to a software module 310 comprising computer-executable code for computing whichever of the parameters $\mu_{1P}, \mu_{1T}, \sigma_P, \sigma_T, \mu_{3T}, \mu_{4P}, \mu_{4T}$ are to used in the chosen algorithm for calculating the compliance factor K. Even moderately skilled programmers will know how to design this software module 310.

The patient-specific data such as age, height, weight, BSA, etc., is stored in a memory region 315, which may also store other predetermined parameters such as $K_{prior}$. These values may be entered using any known input device 400 in the conventional manner.

A compliance calculation module 320, also comprising computer-executable code, then takes as inputs the various moment and patient-specific values and performs the chosen calculations for computing the compliance factor. For example, the module 320 could enter the parameters into the expression given above for K, or into some other expression derived by creating an approximating function that best fits a set of test data. The calculation module 320 preferably also selects the time window [t0, tf] over which each compliance, SV and/or CO estimate is generated. This may be done as simply as choosing which and how many of the stored, consecutive, discretized P(t) values P(k) are used in each calculation, which is the same as selecting n in the range k=0, . . . , (n−1).

Taking K, $\sigma_P$ and $\mu_{4P}$ as inputs, a stroke volume computation module 330, again comprising computer-executable code in which the scaling factor γ may be pre-encoded, then computes the improved SV estimate as explained above. Taking as inputs both SV and a heart rate value HR generated by any known hardware device 340 or software routine (for example, using Fourier or derivative analysis) for measuring heart rate, a CO computation module 330 may then generate an estimate of CO using, for example, the standard formula CO=SV*HR.

Additional software modules 360 and 370 may be included to perform the calculations described above to estimate the exponential pressure decay constant tau and vascular resistance R.

As shown in FIG. 3, the software modules 320, 330, 350, 360, and 370, that is, whichever of these are included, may be implemented within an estimation software component 317, which may of course be combined with the moment-calculating component 310, or with other software components of the processing system 300 as desired.

As mentioned above, it is not necessary for the system according to the invention to compute SV or CO if these values are not of interest. The same is true for tau and R. In such case, the corresponding software modules will of course not be needed and may be omitted. For example, the invention could be used in a study of arterial compliance itself. Nonetheless, as FIG. 3 illustrates, any or all of the results K, SV, CO, tau and R may be passed to any conventional display or recording device 500 for presentation to and interpretation by a user. As with the input device 400, the display 500 will typically be the same as is used by the processing system for other purposes.

The invention further relates to a computer program loadable in a computer unit or the processing system 300 in order to execute the method of the invention. Moreover, the various software modules 310, 315, 320, 330, 340, 350, 360, and 370 used to perform the various calculations and perform related method steps according to the invention may also be stored as computer-executable instructions on a computer-readable medium in order to allow the invention to be loaded into and executed by different processing systems.

Other Outputs

The invention is described above in the context of calculating estimates of SV and CO. This is the use of invention that the inventor assumes will be most common, but the invention is not inherently limited to such use. In essence, the invention provides a novel way to calculate a compliance factor K (or C) and therefore any parameter that is a function of (for example, proportional to) K, not just CO. Consequently, the advantages of the invention will also apply to the calculation of any other cardiovascular value derived from K, such as tau, R, etc.

What is claimed is:

1. A method for determining a cardiovascular parameter of a subject comprising:
   sensing an input signal that indicates arterial blood pressure;
   calculating at least one statistical moment of a first function of the input signal having an order of two or higher; and
   estimating the cardiovascular parameter as a second function of at least one statistical moment of a first function of the input signal having an order greater than one.

2. A method as in claim 1, in which the cardiovascular parameter is arterial compliance.

3. A method as in claim 1, in which the cardiovascular parameter is vascular resistance.

4. A method as in claim 1, in which the cardiovascular parameter is cardiac output.

5. A method as in claim 1, in which the cardiovascular parameter is stroke volume.

6. A method as in claim 1, in which the cardiovascular parameter is a pressure decay constant.

7. A method as in claim 1, in which the step of estimating the cardiovascular parameter comprises computing the statistical moment(s) of a sequence of measured arterial pressure values.

8. A method as in claim 7, further comprising estimating the cardiovascular parameter as a function of the kurtosis of the input signal.

9. A method as in claim 7, further comprising estimating the cardiovascular parameter as a function of the skewness of the input signal.

10. A method as in claim 7, further comprising:
    measuring a predetermined set of anthropometric parameters of the subject; and
    estimating the cardiovascular parameter as a function of the measured anthropometric parameters.

11. A method as in claim 7, in which the cardiovascular parameter is arterial compliance.

12. A method as in claim 7, in which the cardiovascular parameter is vascular resistance.

13. A method as in claim 7, further comprising:
    computing both the standard deviation and at least one statistical moment, having an order greater than two, of the input signal;
    estimating an arterial compliance value as a function of at least the statistical moment of the input signal having an order greater than two; and
    computing an estimate of stroke volume as a function of the product of the standard deviation and the arterial compliance value.

14. A method as in claim 13, further comprising:
    computing the kurtosis of the input signal;
    computing an estimate of stroke volume as a function not only of the product of the standard deviation and the arterial compliance value, but also of an offset factor that is proportional to the kurtosis.

15. A method as in claim 7, further comprising:
    measuring the subject's heart rate;
    computing both the mean and the standard deviation of the input signal;
    computing, as the cardiovascular parameter, a pressure decay constant a function that is proportional to the mean and inversely proportion to both the standard deviation and the heart rate.

16. A method as in claim 15, further comprising:
    computing an arterial compliance value; and
    computing, as the cardiovascular parameter, a vascular resistance value as a function that is proportional to the pressure decay constant and inversely proportion to the arterial compliance value.

17. A method as in claim 7, in which the cardiovascular parameter is arterial compliance, further comprising:
    determining an approximating function relating a set of clinically determined reference measurements to arterial compliance, in which the approximating function is a function of at least three different statistical moments of the input signal, as well as of a set of anthropometric values;
    computing the three different statistical moments of the input signal, as well as measuring the set of anthropometric values of the subject;
    estimating the arterial compliance of the subject by evaluating the approximating function with the computed three different statistical moments of the input signal, as well as the measured set of anthropometric values of the subject.

18. A method as in claim 17, further comprising:
sensing the input signal over a period corresponding to at least one cardiac cycle; and
computing a set of pressure-weighted time values, each corresponding to the product of a sensing time, relative to an initial time, and arterial pressure at the sensing time;
in which the approximating function is a function also of the statistical moment(s) of the set of pressure-weighted time values.

19. A method as in claim 17, further comprising computing at least two statistical moments not only of the input signal, but also of the set of pressure-weighted time values;
in which the approximating function is a function of the computed statistical moments of both the input signal and of the set of pressure-weighted time values.

20. A method as in claim 17, further comprising:
measuring the subject's heart rate;
estimating stroke volume as a function of the product of the estimated arterial compliance and the standard deviation of the input signal; and
computing cardiac output value as a function of the product of the estimated stroke volume and the measured heart rate.

21. A method as in claim 1, further including the step of sensing the input signal over a period corresponding to at least one cardiac cycle, and in which the step of estimating the cardiovascular parameter comprises
computing a set of pressure-weighted time values, each corresponding to the product of a sensing time, relative to an initial time, and arterial pressure at the sensing time; and
computing the statistical moment(s) of the pressure-weighted time values.

22. A method as in claim 21, in which the cardiovascular parameter is arterial compliance.

23. A method as in claim 21, in which the cardiovascular parameter is vascular resistance.

24. A method as in claim 21, in which the cardiovascular parameter is cardiac output.

25. A method as in claim 21, in which the cardiovascular parameter is stroke volume.

26. A method as in claim 21, in which the cardiovascular parameter is a pressure decay constant.

27. A method as in claim 21, further comprising estimating the cardiovascular parameter as a function of the kurtosis of the pressure-weighted time values.

28. A method as in claim 21, further comprising estimating the cardiovascular parameter as a function of the standard deviation of the pressure-weighted time values.

29. A method as in claim 21, further comprising estimating the cardiovascular parameter as a function of the skewness of the pressure-weighted time values.

30. A method as in claim 21, further comprising:
measuring a predetermined set of anthropometric parameters of the subject; and
estimating the cardiovascular parameter as a function of the measured anthropometric parameters.

31. A method as in claim 21, in which the cardiovascular parameter is arterial compliance, further comprising:
determining an approximating function relating a set of clinically determined reference measurements to arterial compliance, in which the approximating function is a function of the statistical moment(s) of the pressure-weighted time values and of a set of anthropometric values;
computing the statistical moment(s) of the pressure-weighted time values, as well as measuring the set of anthropometric values of the subject;
estimating the arterial compliance of the subject by evaluating the approximating function with the computed statistical moment(s) of the pressure-weighted time values, as well as with the measured set of anthropometric values of the subject.

32. A method as in claim 1, further comprising:
sensing the input signal over a period corresponding to at least one cardiac cycle, and in which the step of estimating the cardiovascular parameter comprises;
computing at least one statistical moment of a sequence of measured arterial pressure values;
computing a set of pressure-weighted time values, each corresponding to the product of a sensing time, relative to an initial time, and arterial pressure at the sensing time; and
computing at least one statistical moment of the set of pressure-weighted time values;
estimating the cardiovascular parameter as function of both the statistical moment(s) of the sequence of measured arterial pressure values and the statistical moment(s) of the set of pressure-weighted time values.

33. A method as in claim 32, further comprising:
measuring a predetermined set of anthropometric parameters of the subject; and
estimating the cardiovascular parameter as a function also of the measured anthropometric parameters.

34. A method as in claim 32, in which the cardiovascular parameter is arterial compliance.

35. A method as in claim 34, further comprising:
measuring a predetermined set of anthropometric parameters of the subject; and
determining an approximating function relating a set of clinically determined reference measurements to arterial compliance, in which the approximating function is a function of at least the statistical moment(s) of the sequence of measured arterial pressure values, of the statistical moment(s) of the set of pressure-weighted time values, and of the set of anthropometric values;
estimating the arterial compliance of the subject by evaluating the approximating function with the statistical moment(s) of the sequence of measured arterial pressure values, of the statistical moment(s) of the set of pressure-weighted time values, and of the set of anthropometric values, all of the subject.

36. A method as in claim 32, in which the cardiovascular parameter is vascular resistance.

37. A method for determining cardiac stroke volume comprising:
sensing an input signal that indicates arterial blood pressure of a subject;
calculating the standard deviation and kurtosis of the input signal;
determining an arterial compliance value of the subject;
computing an estimate of stroke volume as a function of the product of the standard deviation and the arterial compliance value, as well as of an offset factor that is proportional to the kurtosis.

38. A method as in claim 37, in which the offset factor is $\gamma(\mu_4 3)$, where $\gamma$ is a predetermined constant and $\mu_4$ is the kurtosis.

39. A system for determining a cardiovascular parameter of a subject comprising:
a monitoring system sensing an input signal that indicates arterial blood pressure and including a processing system including:
a moment-calculating module comprising computer-executable code for calculating at least one statistical moment of a first function of the input signal having an order of two or higher; and
an estimation module comprising computer-executable code for estimating the cardiovascular parameter as a second function of at least one statistical moment of a first function of the input signal having an order greater than one.

40. A system as in claim 39, in which the cardiovascular parameter is arterial compliance.

41. A system as in claim 39, in which the cardiovascular parameter is vascular resistance.

42. A system as in claim 39, in which the cardiovascular parameter is cardiac output.

43. A system as in claim 39, in which the cardiovascular parameter is stroke volume.

44. A system as in claim 39, in which the cardiovascular parameter is pressure decay constant.

45. A system as in claim 39, in which the estimation module further comprises computer-executable code for estimating the cardiovascular parameter by computing the statistical moment(s) of a sequence of measured arterial pressure values.

46. A system as in claim 39, in which the estimation module further comprises computer-executable code for estimating the cardiovascular parameter as a function of the kurtosis of the input signal.

47. A system as in claim 39, in which the estimation module further comprises computer-executable code for estimating the cardiovascular parameter as a function of the skewness of the input signal.

48. A system as in claim 45, further comprising:
an input arrangement for inputting to the processing system a predetermined set of anthropometric parameters of the subject;
the estimation module including additional computer-executable code for estimating the cardiovascular parameter as a function also of the measured anthropometric parameters.

49. A system as in claim 45, in which the cardiovascular parameter is arterial compliance.

50. A system as in claim 45, in which the cardiovascular parameter is vascular resistance.

51. A system as in claim 45, in which
the moment-calculating module comprises further computer-executable code for computing both the standard deviation and at least one statistical moment, having an order greater than two, of the input signal; and
the estimation module comprises further computer-executable code for estimating an arterial compliance value as a function of at least the statistical moment of the input signal having an order greater than two; and for computing an estimate of stroke volume as a function of the product of the standard deviation and the arterial compliance value.

52. A system as in claim 1, further comprising:
the moment-calculating module comprises further computer-executable code for computing the kurtosis of the input signal;
the estimation module comprises further computer-executable code computing an estimate of stroke volume as a function not only of the product of the standard deviation and the arterial compliance value, but also of an offset factor that is proportional to the kurtosis.

53. A system as in claim 45, further comprising:
a heart rate monitor measuring the subject's heart rate;
in which
the moment-calculating module comprises further computer-executable code for computing both the mean and the standard deviation of the input signal;
the estimation module comprises further computer-executable code for computing, as the cardiovascular parameter, a pressure decay constant a function that is proportional to the mean and inversely proportion to both the standard deviation and the heart rate.

54. A system as in claim 53, in which
the moment-calculating module comprises further computer-executable code for computing an arterial compliance value; and for computing, as the cardiovascular parameter, a vascular resistance value as a function that is proportional to the pressure decay constant and inversely proportion to the arterial compliance value.

55. A system as in claim 45, in which the cardiovascular parameter is arterial compliance, in which:
the moment-calculating module comprises further computer-executable code for computing at least three different statistical moments of the input signal;
the estimation module comprises further computer-executable code for estimating the arterial compliance of the subject by evaluating an approximating function with the computed three different statistical moments of the input signal, as well with a measured set of anthropometric values of the subject;
the approximating function relating a set of clinically determined reference measurements to arterial compliance, the reference measurements including the at least three different statistical moments and the set of anthropometric values.

56. A system as in claim 55, in which:
the processing system is provided for sensing the input signal over a period corresponding to at least one cardiac cycle and includes computer-executable code for computing a set of pressure-weighted time values, each corresponding to the product of a sensing time, relative to an initial time, and arterial pressure at the sensing time;
the moment-calculating module comprises further computer-executable code for computing at least one statistical moment of the set of pressure-weighted time values;
the approximating function is a function also of the statistical moment(s) of the set of pressure-weighted time values.

57. A system as in claim 55, further comprising computing at least two statistical moments not only of the input signal, but also of the set of pressure-weighted time values;
in which the approximating function is a function of the computed statistical moments of both the input signal and of the set of pressure-weighted time values.

58. A method as in claim 55, further comprising:
a heart rate measuring arrangement providing a signal indicating the subject's heart rate;
in which:
the estimation module comprises further computer-executable code for estimating stroke volume as a function of the product of the estimated arterial compliance and the standard deviation of the input signal; and for computing cardiac output value as a function of the product of the estimated stroke volume and the measured heart rate.

59. A system as in claim 39, in which:
the processing system is provided for sensing the input signal over a period corresponding to at least one cardiac cycle;
the moment-calculating module comprises further computer-executable code for computing a set of pressure-weighted time values, each corresponding to the product of a sensing time, relative to an initial time, and arterial pressure at the sensing time; and for computing the statistical moment(s) of the pressure-weighted time values.

60. A system as in claim 59, in which the cardiovascular parameter is arterial compliance.

61. A system as in claim 59, in which the cardiovascular parameter is vascular resistance.

62. A system as in claim 59, in which the cardiovascular parameter is cardiac output.

63. A system as in claim 59, in which the cardiovascular parameter is stroke volume.

64. A system as in claim 59, in which the cardiovascular parameter is a pressure decay constant.

65. A system as in claim 59, in which
the moment-calculating module comprises further computer-executable code for computing the kurtosis of the set of pressure-weighted time values; and
the estimation module comprises further computer-executable code for estimating the cardiovascular parameter as a function of the kurtosis of the pressure-weighted time values.

66. A system as in claim 59, in which
the moment-calculating module comprises further computer-executable code for computing the standard deviation of the set of pressure-weighted time values; and
the estimation module comprises further computer-executable code for estimating the cardiovascular parameter as a function of the standard deviation of the pressure-weighted time values.

67. A system as in claim 59, in which:
the moment-calculating module comprises further computer-executable code for computing the skewness of the set of pressure-weighted time values; and
the estimation module comprises further computer-executable code for estimating the cardiovascular parameter as a function of the skewness of the pressure-weighted time values.

68. A system as in claim 59, further comprising:
an input arrangement for inputting to the processing system a predetermined set of anthropometric parameters of the subject;
the estimation module including additional computer-executable code for estimating the cardiovascular parameter as a function also of the measured anthropometric parameters.

69. A system as in claim 59, in which the cardiovascular parameter is arterial compliance, in which:
the moment-calculating module comprises further computer-executable code for computing at least three different statistical moments of the pressure-weighted time values;
the estimation module comprises further computer-executable code for estimating the arterial compliance of the subject by evaluating an approximating function with the computed three different statistical moments of the pressure-weighted time values, as well with a measured set of anthropometric values of the subject;
the approximating function relating a set of clinically determined reference measurements to arterial compliance, the reference measurements including the at least three different statistical moments and the set of anthropometric values.

70. A system as in claim 39, in which the moment-calculating module and the estimation module are implemented as a single body of computer-executable code.

71. A system as in claim 39, in which:
the processing system is provided for sensing the input signal over a period corresponding to at least one cardiac cycle;
the moment-calculating module comprises further computer-executable code
for computing at least one statistical moment of a sequence of measured arterial pressure values;
for computing a set of pressure-weighted time values, each corresponding to the product of a sensing time, relative to an initial time, and arterial pressure at the sensing time; and
for computing at least one statistical moment of the pressure-weighted time values;
the estimation module comprises further computer-executable code for estimating the cardiovascular parameter as function of both the statistical moment(s) of the sequence of measured arterial pressure values and the statistical moment(s) of the set of pressure-weighted time values.

72. A system as in claim 71, further comprising an input arrangement for inputting to the processing system a predetermined set of anthropometric parameters of the subject;
the estimation module including additional computer-executable code for estimating the cardiovascular parameter as a function also of the measured anthropometric parameters.

73. A system as in claim 71, in which the cardiovascular parameter is arterial compliance.

74. A system as in claim 73, further comprising:
an input arrangement for inputting to the processing system a predetermined set of anthropometric parameters of the subject;
in which:
the estimation module comprises further computer-executable code for estimating the arterial compliance of the subject by evaluating an approximating function of the statistical moment(s) of the sequence of measured arterial pressure values, of the statistical moment(s) of the set of pressure-weighted time values, and of the set of anthropometric values, the approximating function relating a set of clinically determined reference measurements to arterial compliance, the reference measurements including the at least three different statistical moments and the set of anthropometric values.

75. A system as in claim 71, in which the cardiovascular parameter is vascular resistance.

76. A system for determining cardiac stroke volume comprising:
a processing system sensing an input signal that indicates arterial blood pressure of a subject;
a moment-calculating module comprising computer-executable code for calculating the standard deviation and kurtosis of the input signal;
an estimation module for comprising computer-executable code for determining an arterial compliance value of the subject; and for computing an estimate of stroke volume as a function of the product of the standard deviation and the arterial compliance value, as well as of an offset factor that is proportional to the Kurtosis.

\* \* \* \* \*

UNITED STATES PATENT AND TRADEMARK OFFICE
CERTIFICATE OF CORRECTION

PATENT NO. : 7,452,333 B2  Page 1 of 1
APPLICATION NO. : 10/890887
DATED : November 18, 2008
INVENTOR(S) : Luchy Roteliuk It is certified that error appears in the above-identified patent and that said Letters Patent is hereby corrected as shown below:

Claim 52 should read as follows:

52. A system as in Claim 51, further comprising:

Signed and Sealed this

Twenty-second Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,452,333 B2  
APPLICATION NO. : 10/890887  
DATED : November 18, 2008  
INVENTOR(S) : Luchy Roteliuk Page 1 of 1

It is certified that error appears in the above-identified patent and that said Letters Patent is hereby corrected as shown below:

Column 17, line 62, Claim 52 should read as follows:

52. A system as in Claim 51, further comprising:

This certificate supersedes the Certificate of Correction issued September 22, 2009.

Signed and Sealed this

Twenty-seventh Day of October, 2009

David J. Kappos  
*Director of the United States Patent and Trademark Office*